US011020569B2

(12) United States Patent
Mao

(10) Patent No.: US 11,020,569 B2
(45) Date of Patent: Jun. 1, 2021

(54) NEEDLE PUNCTURE DEVICE

(71) Applicant: Gemtier Medical (Shanghai) Inc., Shanghai (CN)

(72) Inventor: Yaling Mao, Shanghai (CN)

(73) Assignee: Gemtier Medical (Shanghai) Inc., Shanghai (CN)

( * ) Notice: Subject to any disclaimer, the term of this patent is extended or adjusted under 35 U.S.C. 154(b) by 401 days.

(21) Appl. No.: 15/742,417

(22) PCT Filed: Nov. 22, 2016

(86) PCT No.: PCT/CN2016/106819
§ 371 (c)(1),
(2) Date: Jan. 5, 2018

(87) PCT Pub. No.: WO2017/088737
PCT Pub. Date: Jun. 1, 2017

(65) Prior Publication Data
US 2018/0200486 A1    Jul. 19, 2018

(30) Foreign Application Priority Data

Nov. 23, 2015 (CN) .......................... 201510818147.6
Nov. 23, 2015 (CN) .......................... 201520939839.1
Jul. 7, 2016 (CN) .......................... 201610531579.3

(51) Int. Cl.
*A61M 25/06* (2006.01)
*A61M 5/158* (2006.01)
(Continued)

(52) U.S. Cl.
CPC ........ *A61M 25/0612* (2013.01); *A61M 5/158* (2013.01); *A61M 5/1626* (2013.01);
(Continued)

(58) Field of Classification Search
CPC .......... A61M 5/158; A61M 2005/1587; A61M 2005/1585; A61M 2005/1586;
(Continued)

(56) References Cited

U.S. PATENT DOCUMENTS 4,804,372 A    2/1989  Laico et al.
4,946,447 A    8/1990  Hardcastle et al.
(Continued)

FOREIGN PATENT DOCUMENTS

AU    2015336700 B2    1/2017
CA    2803195 A1    1/2012
(Continued)

OTHER PUBLICATIONS

Oxford Dictionary definition for "Portion", available online Dec. 9, 2020 at https://www.lexico.com/en/definition/portion. (Year: 2020).*
(Continued)

*Primary Examiner* — Amber R Stiles
(74) *Attorney, Agent, or Firm* — McCracken & Gillen LLC

(57) ABSTRACT

A needle puncture device comprises: a needle base; a needle; a first structural member disposed outside of the needle base, slidably engaged with the needle base in an extending direction of the needle, and provided with a first restriction mechanism configured to restrict the first structural member from separating from the needle base along the extending direction of the needle; and a second structural member disposed outside of the first structural member, slidably engaged with the first structural member along the extending direction of the needle, and provided with a second restriction mechanism configured to restrict the second structural member from separating from the first structural member along the extending direction of the needle. The present invention has the advantages of both operational conve-
(Continued)

nience for an operator and skin comfort for a patient, and the structural members above the needle base can quickly cover the needle after use.

14 Claims, 10 Drawing Sheets

(51) Int. Cl.
  *A61M 5/162* (2006.01)
  *A61M 5/32* (2006.01)
(52) U.S. Cl.
  CPC ...... *A61M 5/3205* (2013.01); *A61M 25/0631* (2013.01); *A61M 25/0637* (2013.01); *A61M 5/322* (2013.01); *A61M 2005/1581* (2013.01); *A61M 2005/1586* (2013.01)
(58) Field of Classification Search
  CPC ............ A61M 25/0612; A61M 5/1626; A61M 25/0631; A61M 25/0637; A61M 5/3205; A61M 5/322; A61M 2005/1581
  See application file for complete search history.

(56) References Cited

U.S. PATENT DOCUMENTS

| | | | |
|---|---|---|---|
| 5,573,512 | A | 11/1996 | van den Haak |
| 10,265,467 | B2 * | 4/2019 | Mao ............... A61M 5/158 |
| 2003/0073956 | A1 | 4/2003 | Hoffman et al. |
| 2003/0163095 | A1 | 8/2003 | Nakashima |
| 2003/0181869 | A1 * | 9/2003 | Swenson ........... A61M 25/0637 604/263 |
| 2005/0137528 | A1 | 6/2005 | Wilkinson |
| 2006/0178639 | A1 * | 8/2006 | Eric ................... A61M 5/3243 604/192 |
| 2007/0260193 | A1 | 11/2007 | Chin et al. |
| 2012/0179119 | A1 | 7/2012 | Ng et al. |
| 2013/0245564 | A1 * | 9/2013 | Cheng ................ A61M 5/3202 604/195 |

FOREIGN PATENT DOCUMENTS

| | | |
|---|---|---|
| CN | 1148507 | 4/1997 |
| CN | 202478304 | 10/2012 |
| CN | 202590082 | 12/2012 |
| CN | 104288866 | 1/2015 |
| CN | 104288866 A | 1/2015 |
| CN | 204181959 | 3/2015 |
| CN | 204181959 U | 3/2015 |
| CN | 204395141 U | 6/2015 |
| CN | 204410825 | 6/2015 |
| CN | 204410825 U | 6/2015 |
| CN | 204411410 | 6/2015 |
| CN | 204411424 | 6/2015 |
| CN | 205649700 | 10/2016 |
| CN | 106730139 | 5/2017 |
| CN | 107583137 | 1/2018 |
| EP | 1362612 | 11/2003 |
| IR | 80211 | 8/2013 |
| IR | 92362 | 6/2017 |
| JP | 2002000727 | 1/2002 |
| JP | 2007328119 | 12/2007 |
| JP | 2009099070 | 5/2009 |
| JP | 4654102 | 3/2011 |
| TW | 200735907 | 10/2007 |
| TW | 201718045 | 6/2017 |
| TW | 201722488 | 7/2017 |
| WO | WO 03/097150 A2 | 11/2003 |

OTHER PUBLICATIONS

Examination Report No. 2 issued in Australian patent application No. 2016359516 dated Mar. 12, 2019.
Second office Action issued in Canadian patent application No. 2980490 dated Apr. 10, 2019.
Office Action issued in Eurasian patent application No. 201791926/31 dated Apr. 12, 2019.
Canadian First Examination Report dated Jul. 19, 2018, for Canadian Patent Application No. 2,980,490, Applicant, Gemtier Medical (Shanghai) Inc. (7 pages).
Japanese Office Action dated Jul. 30, 2018, for Japanese Patent Application No. 2017-553239, with English Translation, Applicant, Gemtier Medical (Shanghai) Inc. (13 pages).
Non-Final Office Action dated Aug. 9, 2018, for U.S. Appl. No. 15/353,041, Applicant, Gemtier Medical (Shanghai) Inc. (17 pages).
Chinese Search Report and Chinese Office Action with English Translation for Chinese Application No. 2015108181476, Applicant Shanghai Jinta Medical Co., Ltd. (13 pages).
Written Opinion with English Translation for PCT/CN2016/106819, dated Feb. 16, 2017, Applicant, Gemtier Medical (Shanghai) Inc., (14 pages).
Australian Office Action for Australian Application No. 2016359516, dated Apr. 20, 2018, Applicant, Gemtier Medical (Shanghai) Inc. (5 pages).
Search Report with English Translation for PCT/CN2016/105650, dated Dec. 29, 2016. Applicant, Gemtier Medical (Shanghai) Inc. (8 pages).
Written Opinion with English Translation for PCT/CN2016/105650, dated Dec. 29, 2016. Applicant, Gemtier Medical (Shanghai) Inc. (13 pages).
Taiwanese Office Action for TW Application 105137489, with English translation, dated Oct. 21, 2017 (17 pages).
Japanese Office Action for JP Application 2016-218977, with English Translation, dated Sep. 12, 2017 (62 pages).
EESR of European Patent Application 16867960.3, dated Jun. 15, 2018, Applicant, Gemtier Medical (Shanghai) Inc. (7 pages).
Pakistan Office Action for Pakistan Application No. 721/2016, dated Jun. 28, 2018 (2 pages).
Chinese International Search Report with English Translation dated Jan. 20, 2017, for International Application No. PCT/CN/2016/106819, Applicant, Gemtier Medical (Shanghai) Inc. (4 pages).
Search Report issued in the counterpart Argentina patent application No. 20160103595 dated Aug. 24, 2020.
First Examination Report issued in the counterpart India patent application No. 201747031945 dated Sep. 18, 2020.
First Examination Report issued in the counterpart Vietnam patent application No. 1-2018-00007 dated Sep. 29, 2020.
Office Action issued in the counterpart Iranian application No. 139750140003001472 dated Jan. 23, 2020.
Second Examination Report issued in the counterpart GCC application No. GC 2016-32416 dated Mar. 26, 2020.
Feb. 4, 2021 Office Action issued in Singapore Patent Application No. 11201708864R.

* cited by examiner

NEEDLE PUNCTURE DEVICE

CROSS REFERENCE

The present application claims priority of Chinese Patent Applications 201510818147.6 and 201520939839.1 filed on Nov. 23, 2015, and Chinese Patent Application 201610531579.3 filed on Jul. 7, 2016, the contents of which are incorporated herein by reference in their entireties.

FIELD OF INVENTION

The present invention relates to a needle device.

PRIOR ARTS

The needle devices such as intravenous needles in prior arts are usually used once. It is necessary to discard the needle device after use as a medical waste. A needle sleeve is usually added on the needle base to avoid the needle head injuring humans or objects when discarding the needle device. However, the needle devices in prior arts have the defects that the needle sleeve is easy to fall off, which causes exposure of the needle head.

CONTENT OF THE PRESENT INVENTION

The technical problem to be solved in the present invention is for overcoming the defects that the needle sleeve of the needle device in prior arts is easy to fall off, and a needle device is provided.

The present invention solves the above-mentioned technical problems through the following technical solutions:

A needle device, wherein the needle device comprises:

a needle base, having a first side which is close to skin when using;

a needle head, having a first end which is connected to the needle base, the needle head extends parallel to the first side;

a first structure part, the first structure part is arranged outside the needle base and slip matches with the needle base along extension direction of the needle head, a first limit mechanism is arranged between the first structure part and the needle base, the first limit mechanism is adapted to prevent the first structure part being separated from the needle base along extension direction of the needle head;

a second structure part, the second structure part is arranged outside the first structure part and slip matches with the first structure part along extension direction of the needle head, a second limit mechanism is arranged between the first structure part and the second structure part, the second limit mechanism is adapted to prevent the second structure part being separated from the first structure part along extension direction of the needle head;

the first structure part and the second structure part are adapted to slide along the extension direction of the needle head for holding a second end opposite to the first end into the second structure part.

Preferably, the first limit mechanism comprises a first limit structure and a second limit structure respectively formed on the needle base and the first structure part, the first limit structure and the second limit structure are adapted to prevent the first structure part being separated from the needle base along the extension direction of the needle head through mutual match;

or the first limit mechanism comprises a first limit structure and a second limit structure respectively formed on the needle base and the first structure part, the first limit structure and the second limit structure are adapted to prevent the first structure part being separated from the needle base along the extension direction of the needle head through mutual match; the first limit structure and the second limit structure are adapted to lock the first structure part relative to the needle base when the first structure part moves to a first lock position along the extension direction of the needle head.

Preferably, at least one first limit structure is arranged on upper surface of the needle base, the first structure comprises a containing space, at least one elastic limit portion is arranged in the containing space, the elastic limit portion prevents the first limit structure from moving toward fixed end of the elastic limit portion when the first limit structure moves to a position between inner wall of the containing space and free end of the elastic limit portion.

Preferably, the first limit structure is protrusion portion, the containing space is through hole;

or the first limit structure is a protrusion portion, the containing space is a through hole; the first structure part further has a bar groove, the bar groove is communicated with the containing space, the bar groove is located above the protrusion portion;

or the first limit structure is a protrusion portion, the containing space is a through hole; the first structure part further has a bar groove, the bar groove is communicated with the containing space, the bar groove is located above the protrusion portion; the needle device comprises two elastic limit portions, two elastic limit portions are separately located at both sides of the bar groove;

or the first limit structure is a protrusion portion, the containing space is a through hole; the first structure part further has a bar groove, the bar groove is communicated with the containing space, the bar groove is located above the protrusion portion; the needle device comprises two elastic limit portions, two elastic limit portions are separately located at both sides of the bar groove; distance between the free ends of two elastic limit portions is less than distance between the fixed ends of two elastic limit portions;

or the first limit structure is a protrusion portion, the containing space is a through hole; the first structure part further has a bar groove, the bar groove is communicated with the containing space, the bar groove is located above the protrusion portion; the needle device comprises two elastic limit portions, two elastic limit portions are both located at one side of the bar groove; the needle device comprises two protrusion portions, two protrusion portions match with two elastic limit portions respectively;

or the first limit structure is a protrusion portion, the containing space is a through hole; the first structure part further has a bar groove, the bar groove is communicated with the containing space, the bar groove is located above the protrusion portion; the needle device comprises four elastic limit portions, two elastic limit portions are located at one side of the bar groove, and the other two elastic limit portions are located at the other side of the bar groove.

Preferably, the first limit structure has an inclined plane engaging with outer surface of the needle base, the inclined plane locates at a side of the needle base adjacent to the second end of the needle head, the first limit structure has a recess groove at top;

the second limit structure is an elastic limit portion at a side of the first structure part that is away from the second end of the needle head, the elastic limit portion has an elastic limit portion chunk; the inclined plane of the first limit structure is adapted to slip match with the elastic limit portion chunk to elastically deform the elastic limit portion, and the elastic limit portion chunk is adapted to be clamped in the recess groove through elastic recovery of the elastic limit portion.

Preferably, the second limit mechanism comprises a third limit structure and a forth limit structure respectively formed on the first structure part and the second structure part, the third limit structure and the forth limit structure are adapted to prevent the second structure part being separated from the first structure part along the extension direction of the needle head through mutual match;

or the second limit mechanism comprises a third limit structure and a forth limit structure respectively formed on the first structure part and the second structure part, the third limit structure and the forth limit structure are adapted to prevent the second structure part being separated from the first structure part along the extension direction of the needle head through mutual match; the third limit structure and the forth limit structure are adapted to lock the second structure part relative to the first structure part when the second structure part moves to a second lock position along the extension direction of the needle head;

or the second limit mechanism comprises a third limit structure and a forth limit structure respectively formed on the first structure part and the second structure part, the third limit structure and the forth limit structure are adapted to prevent the second structure part being separated from the first structure part along the extension direction of the needle head through mutual match; the third limit structure is a protrusion structure formed on the first structure part, the protrusion structure has an inclined plane engaging with outer surface of the first structure part, the inclined plane locates at a side adjacent to the second end of the needle head, the protrusion structure has a recess groove at top; the forth limit structure is an elastic button at a side of the second structure part that is away from the second end of the needle head, the elastic button has an elastic button chunk; the inclined plane of the button is adapted to slip match with the elastic button chunk to elastically deform the elastic button, and the elastic button chunk is adapted to be clamped in the recess groove of the protrusion structure through elastic recovery of the elastic button.

Preferably, the second limit mechanism comprises a first blocking portion, a second blocking portion, a third blocking portion and an elastic button; the first blocking portion and the second blocking portion are arranged on upper surface of the first structure part, the elastic button is arranged on upper surface of the second structure part, the third blocking portion is arranged on lower surface of the second structure part, the second blocking portion prevents the third blocking portion from further moving when the elastic button moves to a position in front of the first blocking portion.

Preferably, the first structure part is a first sleeve part, the first sleeve part sheathes the needle base; the second structure part is a second sleeve part, the second sleeve part sheathes the first sleeve part;

or length of the needle base is larger than 2 mm, length of the first structure part is larger than 2 mm, and length of the second structure part is larger than 2 mm.

Preferably, the needle base at least comprises an installation portion; the installation portion is a segment of the needle base that may be covered by the first structure part during process of slip match of the first structure part, the first structure part does not exceed first side of the installation portion.

Preferably, the first structure part is opened at first side of the installation portion;

or the installation portion has a top surface which is opposite to the first side and is away from skin when using, the first structure part has a bottom surface which is adjacent to skin when using, the bottom surface of the first structure part is located between the first side of the installation portion and the top surface of the installation portion.

Preferably, the second structure part has a bottom structure which exceeds the first side of the installation portion;

or the second structure part has a bottom structure which exceeds the first side of the installation portion; the second structure part has an opened structure at the first side of the installation portion, the bottom structure is edge of the opened structure of the second structure part;

or the second structure part has a bottom structure which exceeds the first side of the installation portion; a cushion is arranged at bottom of the second structure part, the bottom structure is the cushion, bottom of the cushion is a flat surface, and the installation portion and the first structure part are arranged inside the space surrounded by the second structure part;

or the second structure part has a bottom structure which exceeds the first side of the installation portion; a cushion is arranged at bottom of the second structure part, the bottom structure is the cushion, bottom of the cushion is a flat surface, and the installation portion and the first structure part are arranged inside the space surrounded by the second structure part; a clamping portion is arranged at lower section of the second structure part, and the cushion is clamped by the clamping portion;

or the second structure part has a bottom structure which exceeds the first side of the installation portion; a cushion is arranged at bottom of the second structure part, the bottom structure is the cushion, bottom of the cushion is a flat surface, and the installation portion and the first structure part are arranged inside the space surrounded by the second structure part; the second structure part comprising the cushion is integrally formed;

or the second structure part has a bottom structure which exceeds the first side of the installation portion; a cushion is arranged at bottom of the second structure part, the bottom structure is the cushion, bottom of the cushion is a flat surface, and the installation portion and the first structure part are arranged inside the space surrounded by the second structure part; vertical distance between the needle head and the bottom of the cushion is larger than 0.05 mm;

or the second structure part has a bottom structure which exceeds the first side of the installation portion; the second structure part is a sleeve piece, the second structure part has a flat bottom at the first side of the installation portion, the bottom structure is the flat bottom segment of the second structure part;

or the second structure part has a bottom structure which exceeds the first side of the installation portion; the second structure part is a sleeve piece, the second structure part has a flat bottom at the first side of the installation portion, the bottom structure is the flat bottom segment of the second structure part; external of the flat bottom segment of the second structure part is provided with convex portions extending parallel to the first side, concave portion extending parallel to the first side is formed between adjacent convex portions;

or the second structure part has a bottom structure which exceeds the first side of the installation portion; the bottom structure is soft structure;

or the second structure part has a bottom structure which exceeds the first side of the installation portion; inner wall of the bottom structure slip matches with the first side of the installation portion.

Preferably, a first connection structure and a second connection structure which are mutually slip matched are respectively formed on the needle base and the first structure part; a third connection structure and a forth connection structure which are mutually slip matched are respectively formed on the first structure part and the second structure part;

or a first connection structure and a second connection structure which are mutually slip matched are respectively formed on the needle base and the first structure part; a third connection structure and a forth connection structure which are mutually slip matched are respectively formed on the first structure part and the second structure part; the first connection structure and the second connection structure are respectively a first slide railway and a first slide track which are arranged along the extension direction of the needle head, or the first connection structure and the second connection structure are respectively a first slide track and a first slide railway which are arranged along the extension direction of the needle head, the third connection structure and the forth connection structure are respectively a second slide railway and a second slide track which are arranged along the extension direction of the needle head, or the third connection structure and the forth connection structure are respectively a second slide track and a second slide railway which are arranged along the extension direction of the needle head.

Preferably, a pressing portion is arranged on upper surface of the second structure part.

Preferably, wherein the needle base is provided with an operating handle, the operating handle is provided with at least one wing portion;

or the needle base is provided with an operating handle, the operating handle is provided with at least one wing portion; the needle device comprises one wing portion, the wing portion is located at one side of the needle base;

or the needle base is provided with an operating handle, the operating handle is provided with at least one wing portion; the needle device comprises two wing portions, the wing portions are located at both sides of the needle base separately;

or the needle base is provided with an operating handle, the operating handle is provided with at least one wing portion; the operating handle is sleeved with the needle base, or the operating handle is integrally formed with the needle base, or the operating handle is clamped by the needle base;

or the needle base is provided with an operating handle, the operating handle is provided with at least one wing portion; the operating handle further comprises a bent portion, the bent portion is arranged between the wing portion and the needle base.

Preferably, both of the first structure part and the second structure part are slot shaped;

or the needle device comprises a plurality of first structure parts, the plurality of first structure parts are arranged by layer and are mutually slip matched along the extension direction of the needle head, limit mechanism is arranged between mutual matched first structure parts to prevent the first structure parts being separated along the extension direction of the needle head, an innermost first structure part slip matches with the needle base, an outermost first structure part slip matches with the second structure part;

or the needle device is intravenous needle, blood taking needle, remaining needle or injection needle.

In the present invention, the preferable conditions mentioned above can be arbitrarily combined on the basis of the common sense in the field, and various preferred embodiments of the present invention can be achieved.

The positive effect of the present invention lies in: the needle device of the present invention has advantages that the operator operates conveniently when using, and the skin of patients is comfortable, the needle head can be covered quickly by the structure parts above the needle base after use, and the connection between the structure parts and needle base is tight, the structure parts will not fall off, security of products is improved effectively.

DETAILED DESCRIPTION OF THE PREFERRED EMBODIMENT

Figure 1:
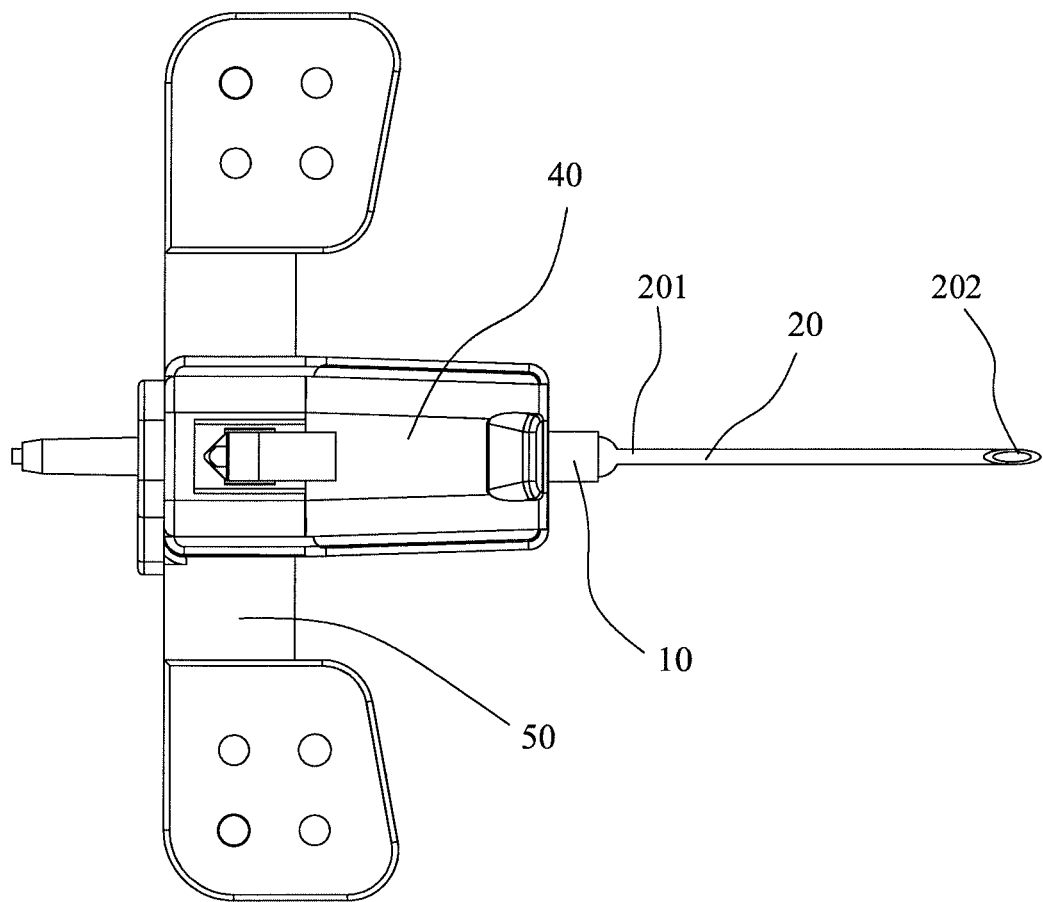
FIG. 1 is a schematic structure view of a preferred embodiment of the present invention.
Figure 2:
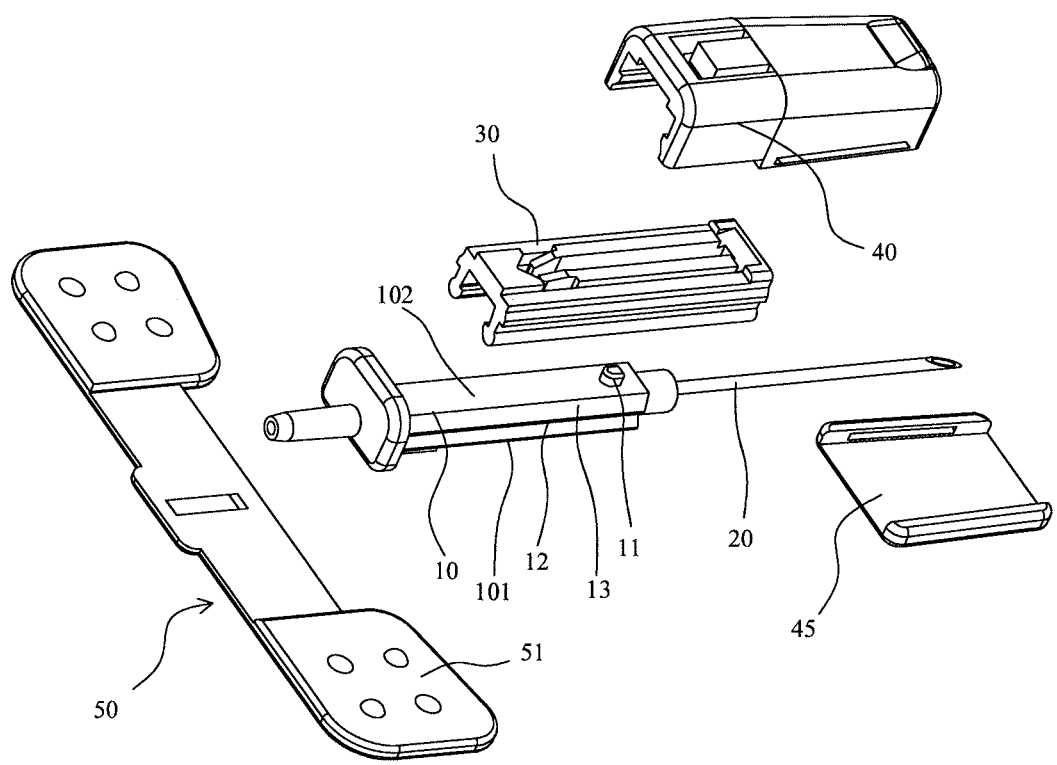
FIG. 2 is a three-dimensional assembly view of a preferred embodiment of the present invention.
Figure 3:
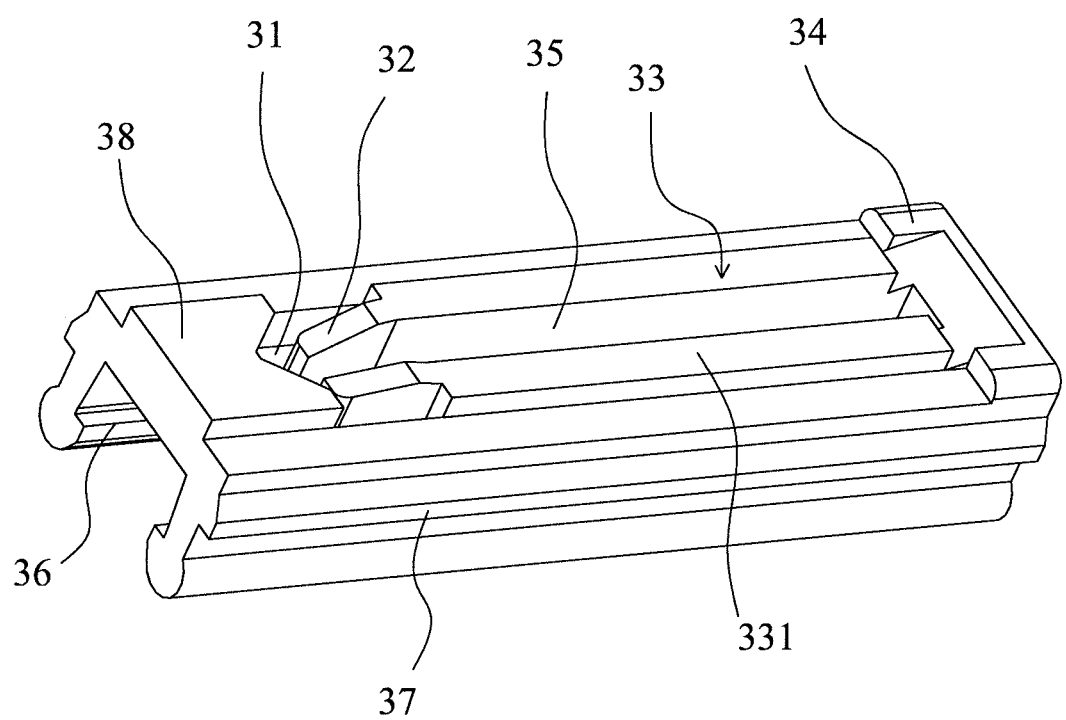
FIG. 3 is a schematic three-dimensional view of the first structure part in a preferred embodiment of the present invention.
Figure 4:
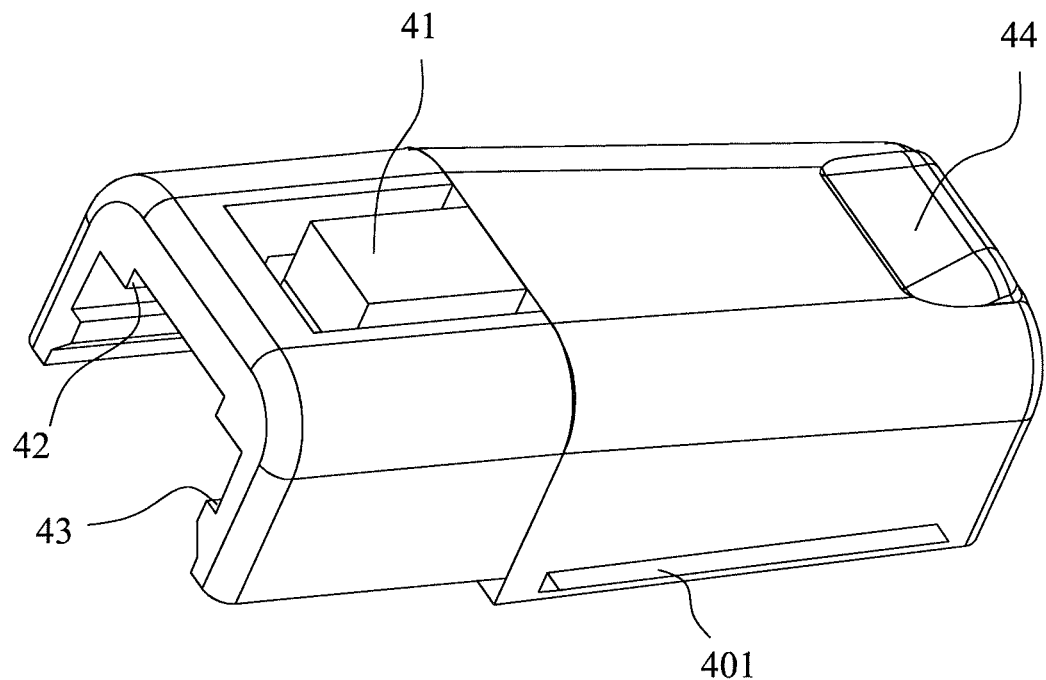
FIG. 4 is a schematic three-dimensional view of the second structure part in a preferred embodiment of the present invention.
Figure 5:
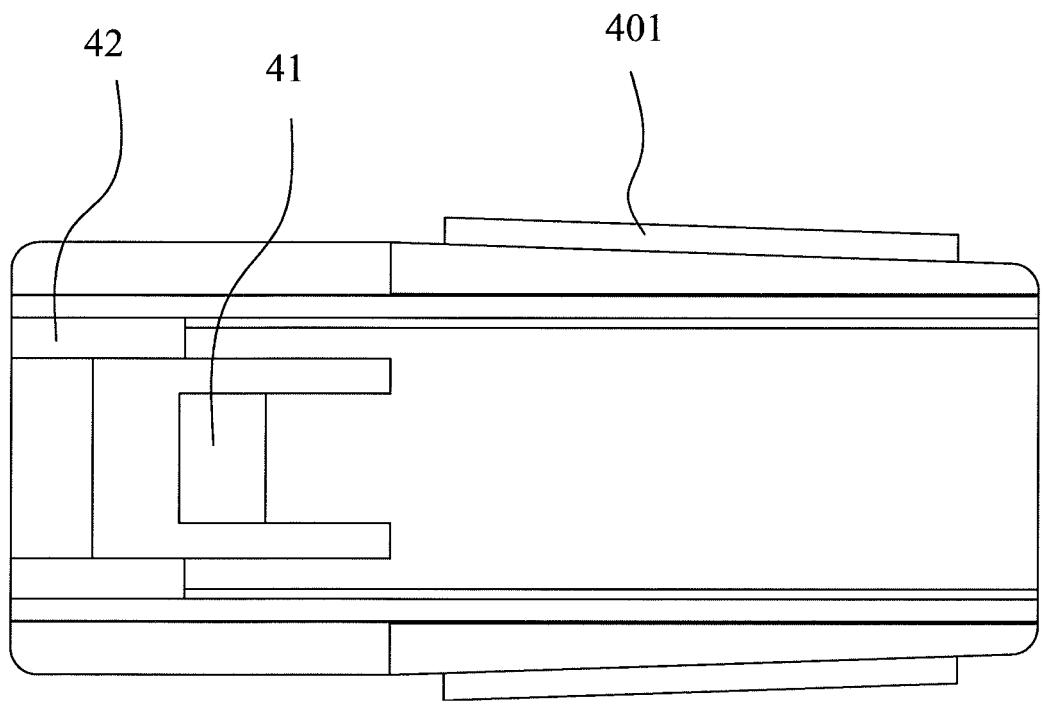
FIG. 5 is a schematic bottom view of the second structure part in a preferred embodiment of the present invention.

Below presents preferred embodiments based on the drawings in order to illustrate the present invention more clearly and completely.

As shown in FIG. 1 to FIG. 10, a needle device, it comprises: a needle base 10, having a first side 101 which is close to skin when using, and a second side 102 which is opposite to the first side 101; a needle head 20, having a first end 201 which is connected to the needle base 10, the needle head 20 extends parallel to the first side 101; a first structure part 30, the first structure part 30 is arranged outside the needle base 10 and slip matches with the needle base 10 along extension direction of the needle head 20, a first limit mechanism is arranged between the first structure part 30 and the needle base 10, the first limit mechanism is adapted to prevent the first structure part 30 being separated from the needle base 10 along extension direction of the needle head 20; a second structure part 40, the second structure part 40 is arranged outside the first structure part 30 and slip matches with the first structure part 30 along extension direction of the needle head 20, a second limit mechanism is arranged between the first structure part 30 and the second structure part 40, the second limit mechanism is adapted to prevent the second structure part 40 being separated from the first structure part 30 along extension direction of the needle head 20; the first structure part 30 and the second structure part 40 are adapted to make a second end 202 which is opposite to the first end 201 be enclosed by the second structure part 40 through sliding along the extension direction of the needle head 20. To protect the second end 202 of the needle head 20, and prevent the second end 202 of the needle head 20 from hurting medical worker.

In the present invention, the first limit mechanism comprises a first limit structure and a second limit structure respectively formed on the needle base 10 and the first structure part 30, the first limit structure and the second limit structure are adapted to prevent the first structure part 30 being separated from the needle base 10 along the extension direction of the needle head 20 through mutual match.

In one embodiment of the present invention, the first limit structure and the second limit structure are adapted to lock the first structure part 30 relative to the needle base 10 when the first structure part 30 moves to a first lock position along the extension direction of the needle head 20

In another embodiment of the present invention, at least one first limit structure is arranged on upper surface of the needle base 10, a containing space 31 is arranged at the first structure part 30, at least one elastic limit portion 32 is arranged in the containing space 31, the elastic limit portion 32 prevents the first limit structure from moving toward fixed end of the elastic limit portion 32 when the first limit structure moves to a position between inner wall of the containing space 31 and free end of the elastic limit portion 32. One side of inner wall of the containing space 31 is fixed limit portion 38. And in said embodiment, the first limit structure is protrusion portion 11, and the containing space 31 is through hole. Such that the connection between the needle base 10 and the first structure part 30 is tight, the first structure part 30 will not rebound.

The first structure part 30 further has a bar groove 35, the bar groove 35 is communicated with the containing space 31, the bar groove 35 is located above the protrusion portion 11. The needle device comprises two elastic limit portions 32, two elastic limit portions 32 are separately located at both sides of the bar groove 35. Distance between the free ends of two elastic limit portions 32 is less than distance between the fixed ends of two elastic limit portions 32.

There may be two elastic limit portions and two protrusion portions, two elastic limit portions are both located at one side of the bar groove, two protrusion portions match with two elastic limit portions respectively. In this way the restriction on the protrusion portion can be improved, to prevent the first structure part rebounding.

There may be four elastic limit portions, two elastic limit portions are located at one side of the bar groove, and the other two elastic limit portions are located at the other side of the bar groove. The increase of the elastic limit portions further improves the restriction on the protrusion portion.

In one further embodiment of the present invention, the first limit structure has an inclined plane engaging with outer surface of the needle base at a side of the needle base that is adjacent to the second end of the needle head, the first limit structure has a recess groove at top; the second limit structure is an elastic limit portion at a side of the first structure part that is away from the second end of the needle head, the elastic limit portion has an elastic limit portion chunk; the inclined plane of the first limit structure is adapted to slip match with the elastic limit portion chunk to elastically deform the elastic limit portion, and the elastic limit portion chunk is adapted to be clamped in the recess groove through elastic recovery of the elastic limit portion.

When the first structure part slides along the extension direction of the needle head, the elastic limit portion slip matches with the inclined plane of the first limit structure through the elastic limit portion chunk, and the elastic limit portion is elastically deformed, when the elastic limit portion chunk slides into the recess groove of the first limit structure, the elastic limit portion chunk is clamped by the recess groove through elastic recovery of the elastic limit portion, such that the recess groove prevent the elastic limit portion chunk escaping from the recess groove. Such that the connection between the needle base and the first structure part is tight, the first structure part will not rebound.

In one embodiment of the present invention, the second limit mechanism comprises a third limit structure and a forth limit structure respectively formed on the first structure part and the second structure part, the third limit structure and the forth limit structure are adapted to prevent the second structure part being separated from the first structure part along the extension direction of the needle head through mutual match.

The third limit structure and the forth limit structure are adapted to lock the second structure part relative to the first structure part when the second structure part moves to a second lock position along the extension direction of the needle head.

Or the third limit structure is a protrusion structure formed on the first structure part, the protrusion structure has an inclined plane engaging with outer surface of the first structure part at a side that is adjacent to the second end of the needle head, the protrusion structure has a recess groove at top; the forth limit structure is an elastic button at a side of the second structure part that is away from the second end of the needle head, the elastic button has an elastic button chunk; the inclined plane of the button is adapted to slip match with the elastic button chunk to elastically deform the elastic button, and the elastic button chunk is adapted to be clamped in the recess groove of the protrusion structure through elastic recovery of the elastic button.

When the second structure part slides along the extension direction of the needle head, the elastic button slip matches with the inclined plane of the protrusion structure through the elastic button chunk, and the elastic button is elastically deformed, when the elastic button chunk slides into the recess groove, the elastic button chunk is clamped by the recess groove through elastic recovery of the elastic button, such that the recess groove prevent the elastic button chunk escaping from the recess groove. Such that the connection between the second structure part and the first structure part is tight, the second structure part will not rebound.

In another embodiment of the present invention, as shown in FIG. 2 to FIG. 6, the second limit mechanism comprises a first blocking portion 33, a second blocking portion 34, a third blocking portion 42 and an elastic button 41; the first blocking portion 33 and the second blocking portion 34 are arranged on upper surface of the first structure part 30, the elastic button 41 is arranged on upper surface of the second structure part 40, the third blocking portion 42 is arranged on lower surface of the second structure part 40, the second blocking portion 34 prevents the third blocking portion 42 from further moving when the elastic button 41 moves to a position in front of the first blocking portion 33. Such that the connection between the second structure part 40 and the first structure part 30 is tight, the second structure part 40 will not rebound.

The first blocking portion 33 comprises two strip portions 331, the strip portions 331 are arranged on upper surface of the first structure part 30, two strip portions 331 are arranged to be parallel to each other, and the strip portions 331 act as a sliding track of the third blocking portion 42.

In one embodiment of the present invention, the first structure part 30 is a first sleeve part, the first sleeve part sheathes the needle base; the second structure part 40 is a second sleeve part, the second sleeve part sheathes the first sleeve part.

In one embodiment of the present invention, the needle base 10 at least comprises an installation portion 13; the installation portion 13 is a segment of the needle base 10 that may be covered by the first structure part 30 during process of slip match of the first structure part 30. The installation portion 13 is one segment of the needle base 10, the installation portion 13 may be integrally or separately arranged with the needle base 10. The first structure part 30 does not exceed first side 101 of the installation portion 13. The first structure part 30 is opened at first side 101 of the installation portion 13. The second structure part 40 has a bottom structure which exceeds the first side 101 of the installation portion 13, i.e., the second structure part 40 has a bottom structure which exceeds the first side 101 of the installation portion 13 along the direction from the second side 102 to the first side 101.

When pulling the needle head 20 outward, the second structure part 40 is pressed, the bottom structure of the second structure part 40 contacts with the skin of patient to form a support, so as to pull the needle head 20 outward easily, the bottom structure may enable a distance or a barrier to be existed between the first side 101 of the installation portion 13 and the skin, the installation portion 13 may be pulled smoothly, adhesion generated by contacting between the installation portion 13 and the skin for a long time may be avoided, the patient's keenly feel produced because the installation portion 13 drags the skin when pulling the needle head 20 is avoided.

And because the first structure part 30 does not exceed first side 101 of the installation portion 13, the first structure part 30 is unable to increase the distance between the first side 101 of the installation portion 13 and the second structure part 40 located at the first side 101 of the installation portion 13, to decrease the distance between the first side 101 of the installation portion 13 and the second structure part 40 as most as possible, to reduce diameter of the segment at the installation portion 13 when the first structure part 30 and the second structure part 40 are retracted as most as possible, to reduce inclined angle of the needle head 20 to the skin as most as possible, thereby improving comfort level of the patient during infusion.

Inner wall of the bottom structure slip matches with the first side 101 of the installation portion 13. The distance between the installation portion 13 and the inner wall of the bottom structure of the second structure part 40 may be eliminated, to decrease the distance between the installation portion 13 and the patient's skin as most as possible, thereby more effectively decreasing inclined angle of the needle head 20 to the skin, and improving comfort level of the patient during infusion. Preferably, the bottom structure is soft structure, such that the bottom structure more fits with the patient's skin, thereby further improving the comfort level of the patient.

In one further embodiment of the present invention, the first structure part 30 sheathes the installation portion 13, the first structure part 30 may be plate shaped structure or slot type structure with any shape, is preferably n type or c type, to enclose the needle head 20 as most as possible, to prevent the needle head 20 from contacting with the operator, thereby avoiding accidental injury. Simultaneously, it is unable to increase the distance between the installation portion 13 and the skin. And the first structure part has an opened structure at the first side 101 of the installation portion 13, the first structure part 30 of opened structure may cover circumferential segments of the needle head 20 after being pulled toward the needle head 20, to better prevent the needle head 20 from contacting with the medical worker, thereby avoiding disease spread. That is to say, only the segment of the first structure part 30 that is able to increase the distance between the first side 101 of the installation portion 13 and the second structure part 40 is removed, the distance between the first side 101 of the installation portion 13 and the skin may be decreased. The second structure part 40 sheathes the first structure part 30. When using the needle device, the first structure part 30 and the second structure part 40 are arranged on the installation portion 13, after the use of the needle device is finished, pressing the second structure part 40, pulling the needle base 10 and the needle head 20 outward, the installation portion 13 is pulled out from the first structure part 30, and the first structure part 30 is pulled out from the second structure part 40, until the second structure part 40 cover the second end 202 which is opposite to the first end 201 of the needle head 20, it may be able to prevent the needle hurting the recovery worker during recovery, simultaneously, the comfort level of the patient won't be influenced during using process. The second structure part 40 may be slot type structure with any shape.

The installation portion 13 has a top surface which is opposite to the first side 101 and is away from skin when using, the first structure part 30 has a bottom surface which is adjacent to skin when using, the bottom surface of the first structure part 30 is located between the first side 101 of the installation portion 13 and the top surface of the installation portion 13. The top surface of the installation portion 13 is the second side 102 of the installation portion 13, i.e., the bottom surface of the first structure part 30 is located between the first side 101 and the second side 102. Such that the first structure part 30 is completely unable to influence the distance between the first side 101 of the installation portion 13 and the second structure part 40, comfort level of the patient during using process is further improved.

In one embodiment of the present invention, the second structure part 40 has an opened structure at the first side 101 of the installation portion 13, the bottom structure is edge of the opened structure of the second structure part 40; skin supports the edge, there is a certain distance between the installation portion 13 and the skin.

In another embodiment of the present invention, a cushion 45 is arranged at bottom of the second structure part 40, the bottom structure is the cushion 45, bottom of the cushion 45 is a flat surface, that is cushion 45 of flat bottom, and the installation portion 13 and the first structure part 30 are arranged inside the space surrounded by the second structure part 40. The cushion 45 of flat bottom is supported by the skin, causing that there is a barrier between the installation portion 13 and the skin, simultaneously the cushion 45 of flat bottom is adapted to contact with the skin of human, make the skin of patient feel more comfortable when being pressed; the cushion 45 enlarges contacting area of the second structure part 40 and the skin, comfort level of the patient is further improved, the patient's keenly fell produced by rolling of the second structure part 40 is avoided when pressing. The installation portion 13 and the first structure part 30 are arranged inside the space surrounded by the second structure part 40 comprising the cushion 45. The cushion 45 and other segments of the second structure part 40 may be manufactured separately and then be assembled, at this moment, a clamping portion 401 may be arranged at lower section of the second structure part 40, and the cushion 45 is clamped by the clamping portion 401. In addition, the cushion 45 and other segments of the second structure part 40 can also be integrally formed. Vertical distance between the needle head 20 and the bottom of the cushion 45 is larger than 0.05 mm, preferable 0.1 mm. In this way distance between the needle head 20 and skin of human body can be smaller, so as to improve comfort level of needle device when using. The second structure part 40 comprising the cushion 45 may be cylinder shaped or tube shaped having a polygon cross profile.

In one further embodiment of the present invention, the second structure part 40 is a sleeve piece, the second structure part 40 has a flat bottom at the first side 101 of the installation portion 13, the bottom structure is the flat bottom segment of the second structure part 40.

External of the flat bottom segment of the second structure part 40 is provided with convex portions extending parallel to the first side 101, concave portion extending parallel to the first side 101 is formed between adjacent convex portions. The arrangement of the convex portion and the concave portion causes that it is hard for the second structure part 40 to adjoin and adhere to skin.

In the present invention, a first connection structure and a second connection structure which are mutually slip matched are respectively formed on the needle base 10 and the first structure part 30; a third connection structure and a forth connection structure which are mutually slip matched are respectively formed on the first structure part 30 and the second structure part 40.

The first connection structure and the second connection structure are respectively a first slide railway 12 and a first slide track 36 which are arranged along the extension direction of the needle head 20, or the first connection structure and the second connection structure are respectively a first slide track 36 and a first slide railway 12 which are arranged along the extension direction of the needle head 20, the third connection structure and the forth connection structure are respectively a second slide railway 37 and a second slide track 43 which are arranged along the extension direction of the needle head 20, or the third connection structure and the forth connection structure are respectively a second slide track 43 and a second slide railway 37 which are arranged along the extension direction of the needle head 20.

In one embodiment of the present invention, each of both sides of the needle base 10 has a first slide railway 12, the first structure part 30 has a first slide track 36 matching with the first slide railway 12; each of both sides of the first structure part 30 has a second slide railway 37, the second structure part 40 has a second slide track 43 matching with the second slide railway 37. The arrangement of the slide railway/track is helpful for ensuring stationary of the relative slide among the needle base 10, the first structure part 30 and the second structure part 40.

Both of the first structure part 30 and the second structure part 40 may be slot shaped. Length of the needle base 10 is larger than 2 mm, length of the first structure part 30 is larger than 2 mm, and length of the second structure part 40 is larger than 2 mm.

A pressing portion 44 is arranged on upper surface of the second structure part 40. Such that after use of the needle device, the operator can press the pressing portion 44 on the second structure part 40, to easily slide the second structure part 40.

Figure 6:
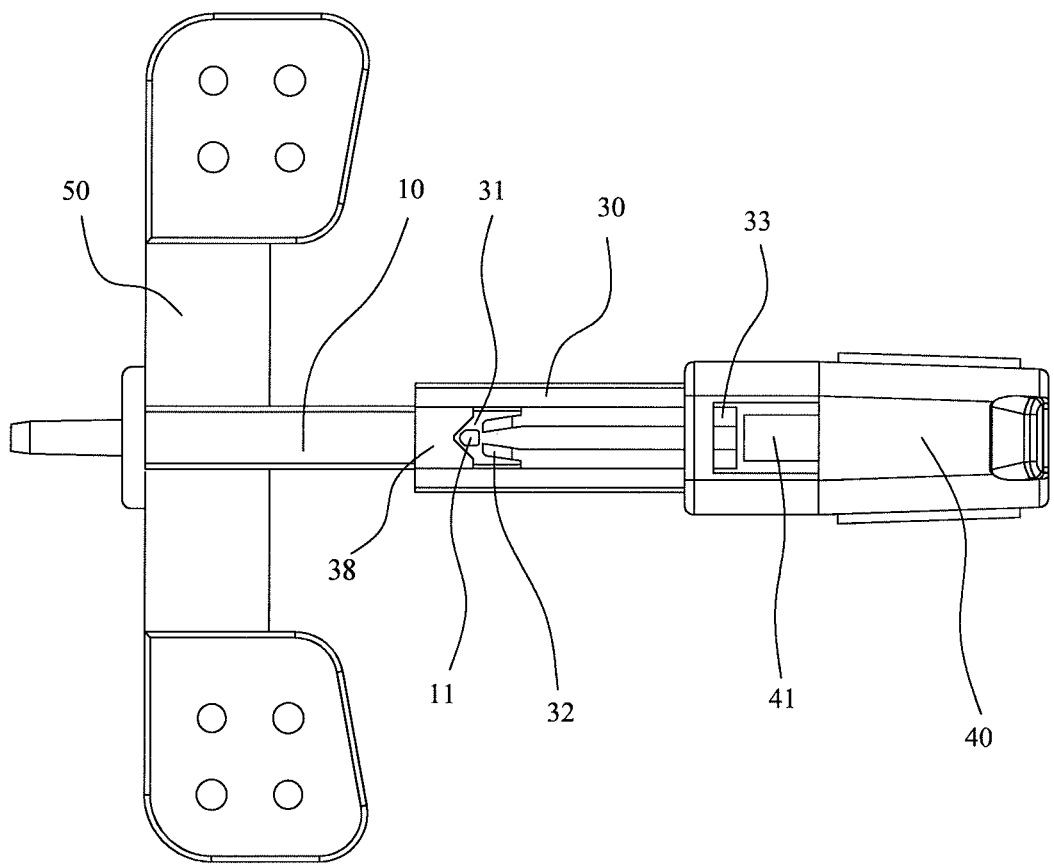
FIG. 6 is a schematic plan view of a preferred embodiment of the present invention after use.
Figure 7:
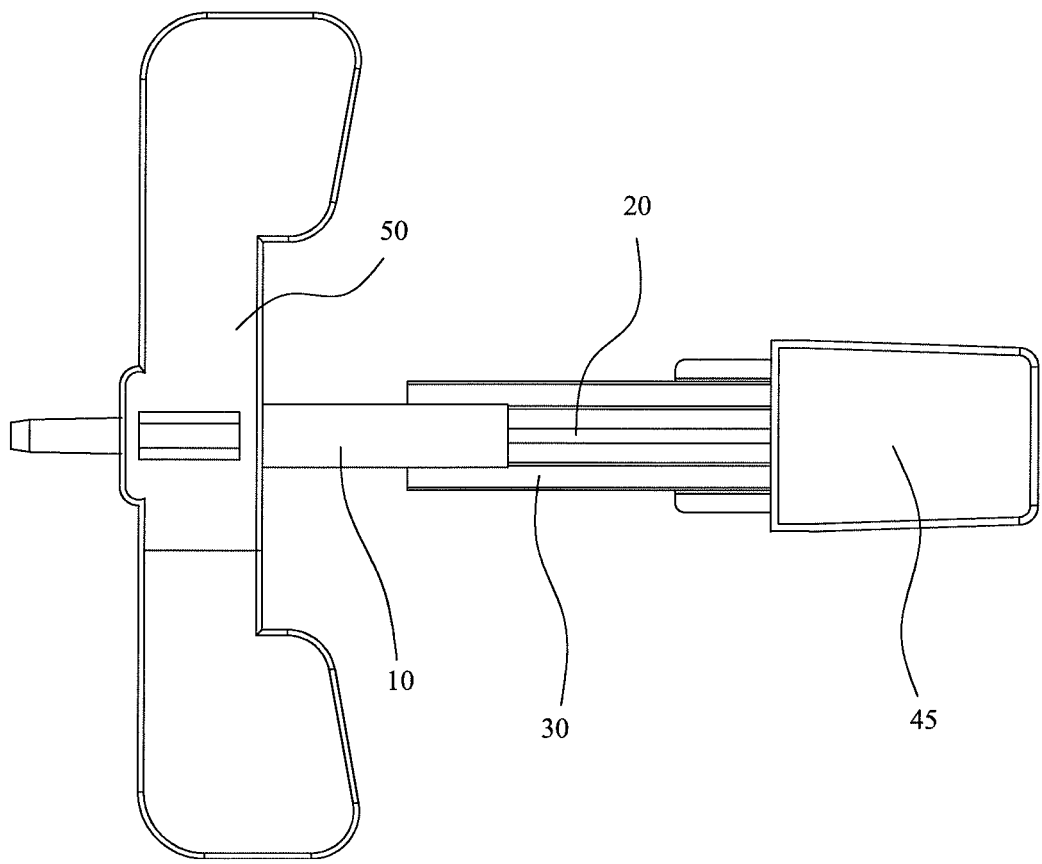
FIG. 7 is a schematic bottom view of a preferred embodiment of the present invention after use.
Figure 8:
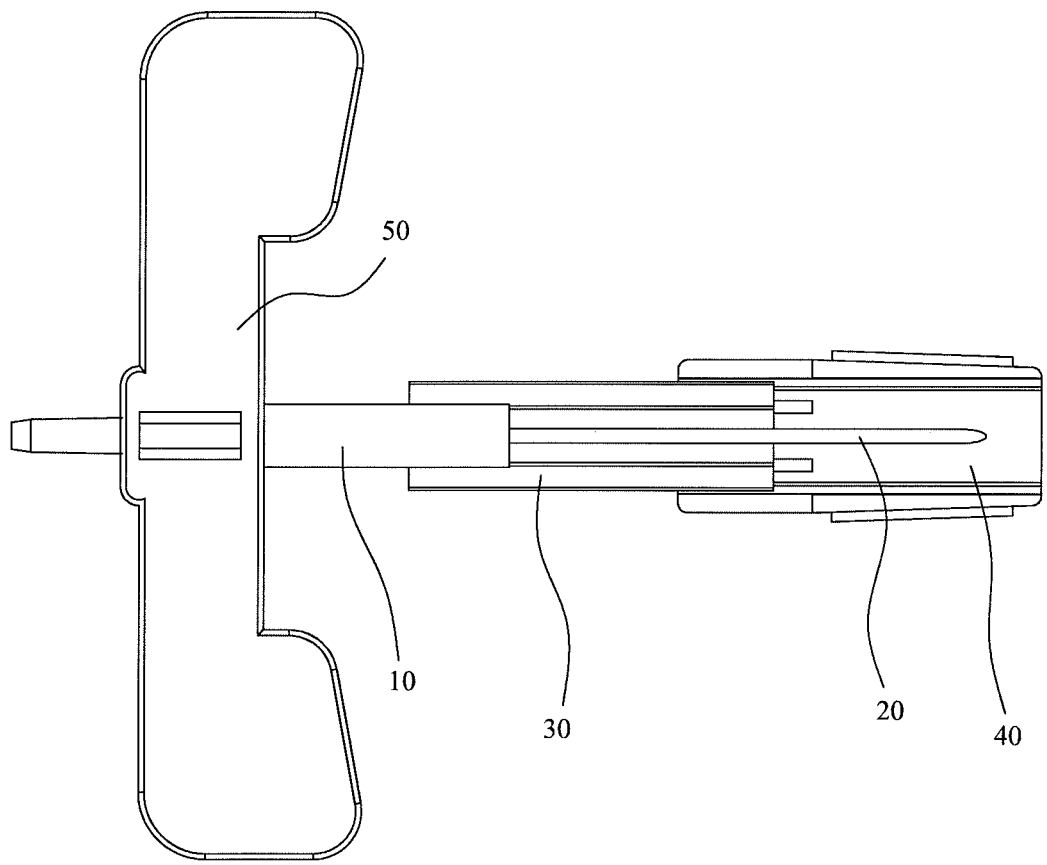
FIG. 8 is a schematic bottom view of a preferred embodiment of the present invention after use when a cushion is not installed.
Figure 9:
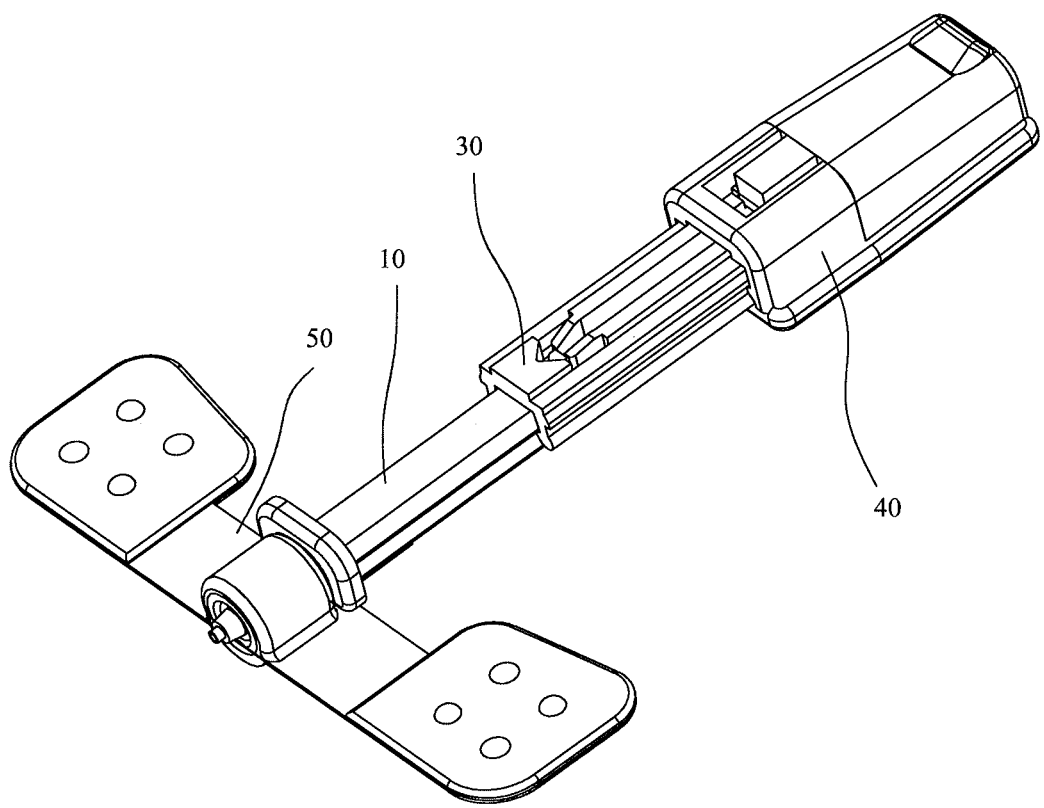
FIG. 9 is a schematic structure view of a preferred embodiment of the present invention when the operating handle is sleeved with the needle base.
Figure 10:
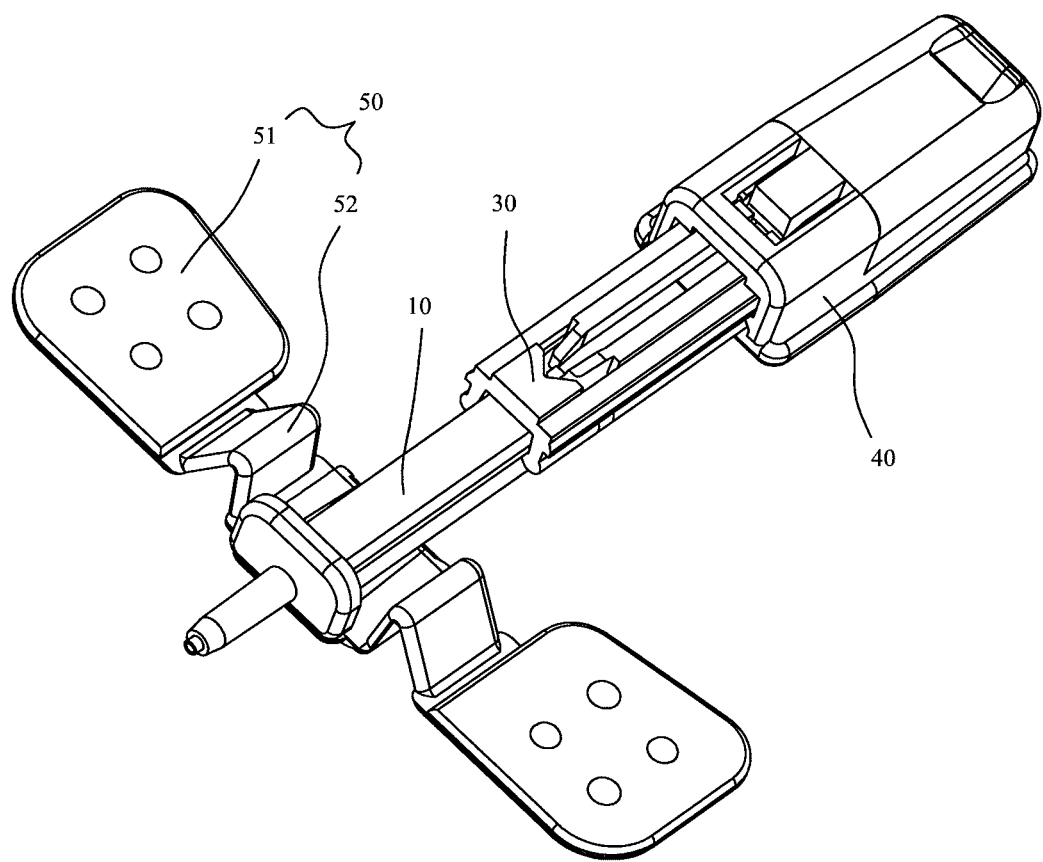
FIG. 10 is a schematic structure view of a preferred embodiment of the present invention when the operating handle has bent portion.

In order to use more conveniently, an operating handle 50 is arranged at the needle base 10, the operating handle 50 is provided with at least one wing portion 51. There may be one wing portion 51, which is located at one side of the needle base 10. There also may be two wing portions 51, and two wing portions 51 are located at both sides of the needle base 10 separately. There may be a variety of methods to connect the operating handle 50 and the needle base 10, and the operating handle 50 can also be integrally formed with the needle base 10; or as shown in FIG. 6, the operating handle 50 is clamped by the needle base 10; or as shown in FIG. 9, the operating handle 50 is sleeved with the needle base 10. As shown in FIG. 10, the operating handle 50 can further comprise a bent portion 52, and the bent portion 52 is arranged between the wing portion 51 and the needle base 10. The operating handle 50 which can be bent is easy to operate.

After use of the needle device, pressing the second structure part 40, pulling the needle base 10 backward, making the needle head 20 leave skin of human body. During the process of backward movement of the needle base 10, the first structure part 30 slides backward with the needle base 10, and the second structure part 40 remains still. When the protrusion portion 11 is restricted by the elastic limit portion 32 inside the containing space 31, the first structure part 30 clamps the needle base 10; when the second blocking portion 34 blocks the third blocking portion 42, the first structure part 30 will not slide backward, and the first blocking portion 33 blocks the elastic button 41, to prevent the first structure part 30 sliding forward. While the first structure part 30 and the second structure part 40 will cover the needle head 20 on the needle base 10. The first structure part 30 and the second structure part 40 will not rebound, which cover the needle head 20 and prevent the needle hurting people or objects. The cushion 45 is a flat surface, which directly contacts with skin of human body, so that the skin of human body will not be uncomfortable in the process of operation, thereby improving comfort level during using process.

The needle device of the present invention has advantages that the operator operates conveniently when using, and the skin of patients is comfortable, the needle head 20 can be covered quickly by the structure parts on the needle base 10 after use, and the connection between the structure parts and needle base 10 is tight, the structure parts will not rebound, security of products is improved effectively.

Figure 11:
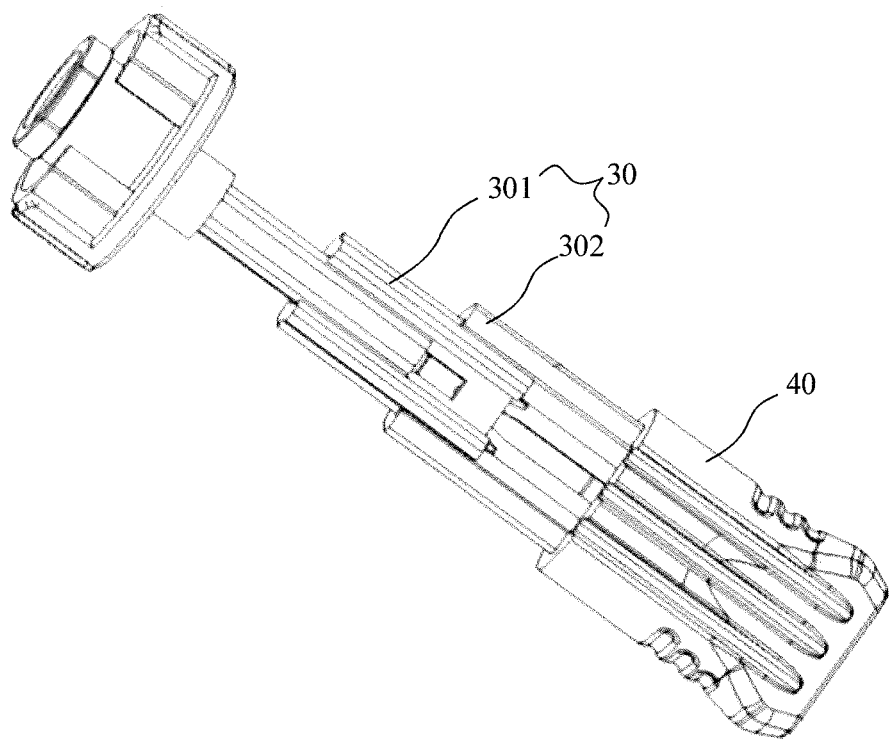
FIG. 11 is a schematic structure view of a preferred embodiment of the present invention when the first structure part has two layers of arrangement.

As shown in FIG. 11, in one embodiment of the present invention, the needle device comprises a plurality of first structure parts 301, 302, the plurality of first structure parts are arranged by three layers and are mutually slip matched along the extension direction of the needle head 20, limit mechanism is arranged between mutual matched first structure parts 301, 302 to prevent the first structure parts being separated along the extension direction of the needle head 20. One of the plurality of first structure parts 301, 302 slip matches with the needle base 10, another one of the plurality of first structure parts slip matches with the second structure part 40, an innermost first structure part 301 slip matches with the needle base 10, an outermost first structure part 302 slip matches with the second structure part 40; the plurality of first structure parts 301, 302 do not exceed the first side 101 of the needle base 10, the arrangement of plurality of first structure parts 301, 302 may decrease the length of the needle base 10 segment, and the plurality of first structure parts may stretch to completely cover the needle head 20 and protect the needle head 20.

The needle device in the present invention may be intravenous needle, blood taking needle, remaining needle, injection needle or other puncture needle, which may improve the comfort level of patient during operation.

In the description of the present invention, it needs to be understand that the directions or position relationships indicated by the term "upper", "lower", "front", "rear", "left", "right", "vertical", "horizontal", "top", "bottom", "inside", "outside" and so on are based on the directions or position relationships shown in the drawings, only in order to facilitate the description of the present invention and the simplified description, rather than indicate or suggest that the described device or unit must have a specific direction, or must be configured or operated in particular direction, accordingly, it cannot be understand as restrictions on the present invention.

Although the specific embodiments of the present invention are illustrated as above, those skilled in the art will appreciate they are exemplary and the protection scope of the present invention is defined by the claims attached. Those skilled in the art can modify or amend these embodiments without deviating the scope and spirit of the present invention, but all of these modifications and amendments are within the protection scope of the present invention.

What is claimed is:

1. A needle device, wherein the needle device comprises:
a needle base, having a first side which is configured to be positioned close to skin during use;
a needle head, having a first end which is connected to the needle base, the needle head extends parallel to the first side;
a first structure part, the first structure part is arranged outside the needle base and slip matches with the needle base along an extension direction of the needle head, a first limit mechanism is arranged between the first structure part and the needle base, the first limit mechanism is adapted to prevent the first structure part from being separated from the needle base along the extension direction of the needle head;
a second structure part, the second structure part is arranged outside the first structure part and slip matches with the first structure part along the extension direction of the needle head, a second limit mechanism is arranged between the first structure part and the second structure part, the second limit mechanism is adapted to prevent the second structure part being separated from the first structure part along the extension direction of the needle head;
the first structure part and the second structure part are adapted to slide along the extension direction of the needle head for holding a second end of the needle head opposite to the first end into the second structure part;
and the needle base at least comprises an installation portion, the installation portion is a segment of the needle base that may be covered by the first structure part during a process of slip matching of the first structure part, the first structure part does not exceed a first side of the installation portion,
wherein the second structure part has a bottom structure that exceeds the first side of the installation portion and an inner wall of the bottom structure slip matches with the first side of the installation portion.

2. The needle device of claim 1, wherein the first limit mechanism comprises a first limit structure and a second limit structure respectively formed on the needle base and the first structure part, the first limit structure and the second limit structure are adapted to prevent the first structure part being separated from the needle base along the extension direction of the needle head through mutual slip matching;
or the first limit mechanism comprises the first limit structure and the second limit structure respectively formed on the needle base and the first structure part, the first limit structure and the second limit structure are adapted to prevent the first structure part being separated from the needle base along the extension direction of the needle head through mutual slip matching and the first limit structure and the second limit structure are adapted to lock the first structure part relative to the needle base when the first structure part moves to a first lock position along the extension direction of the needle head.

3. The needle device of claim 2, wherein the first limit mechanism comprises one or more first limit structures, wherein at least one of the first limit structures is arranged on an upper surface of the needle base, the first structure part comprises a containing space, and at least one elastic limit portion that is arranged in the containing space, the at least one elastic limit portion prevents the first limit structure from moving toward a fixed end of the elastic limit portion when the first limit structure moves to a position between an inner wall of the containing space and the free end of the at least one elastic limit portion.

4. The needle device of claim 3, wherein the at least one first limit structure is a protrusion portion, the containing space is a through hole;
or the at least one first limit structure is the protrusion portion, the containing space is the through hole, and the first structure part further has a bar groove, the bar groove is communicated with the containing space, the bar groove is located above the protrusion portion;
or the at least one first limit structure is the protrusion portion, the containing space is the through hole, and the first structure part further has the bar groove, the bar groove is communicated with the containing space, the bar groove is located above the protrusion portion, and the needle device comprises two elastic limit portions, the two elastic limit portions are separately located at both sides of the bar groove;
or the at least one first limit structure is the protrusion portion, the containing space is the through hole, and the first structure part further has the bar groove, the bar groove is communicated with the containing space, the bar groove is located above the protrusion portion, and the needle device comprises two elastic limit portions, the two elastic limit portions are separately located at both sides of the bar groove, and a distance between free ends of the two elastic limit portions is less than a distance between fixed ends of the two elastic limit portions;
or the at least one first limit structure is the protrusion portion, the containing space is the through hole, and the first structure part further has the bar groove, the bar groove is communicated with the containing space, the bar groove is located above the protrusion portion, and the needle device comprises two elastic limit portions, the two elastic limit portions are both located at one side of the bar groove, and the needle device comprises two protrusion portions, the two protrusion portions match with the two elastic limit portions respectively;

or the at least one first limit structure is the protrusion portion, the containing space is the through hole, and the first structure part further has the bar groove, the bar groove is communicated with the containing space, the bar groove is located above the protrusion portion, and the needle device comprises four elastic limit portions, wherein two elastic limit portions of the four elastic limit portions are located at one side of the bar groove, and the other two elastic limit portions of the four elastic limit portions are located at the other side of the bar groove.

5. The needle device of claim 2, wherein, the first limit structure has an inclined plane engaging with an outer surface of the needle base, the inclined plane located at a side of the needle base adjacent to the second end of the needle head, the first limit structure has a recess groove at a top;

the second limit structure is an elastic limit portion at a side of the first structure part that is away from the second end of the needle head, the elastic limit portion has an elastic limit portion chunk; the inclined plane of the first limit structure is adapted to slip match with the elastic limit portion chunk to elastically deform the elastic limit portion, and the elastic limit portion chunk is adapted to be clamped in the recess groove through elastic recovery of the elastic limit portion.

6. The needle device of claim 1, wherein the second limit mechanism comprises a third limit structure and a fourth limit structure respectively formed on the first structure part and the second structure part, the third limit structure and the fourth limit structure are adapted to prevent the second structure part from being separated from the first structure part along the extension direction of the needle head through mutual slip matching;

or the second limit mechanism comprises the third limit structure and the fourth limit structure respectively formed on the first structure part and the second structure part, the third limit structure and the fourth limit structure are adapted to prevent the second structure part from being separated from the first structure part along the extension direction of the needle head through mutual slip matching; the third limit structure and the fourth limit structure are adapted to lock the second structure part relative to the first structure part when the second structure part moves to a second lock position along the extension direction of the needle head;

or the second limit mechanism comprises the third limit structure and the fourth limit structure respectively formed on the first structure part and the second structure part, the third limit structure and the fourth limit structure are adapted to prevent the second structure part from being separated from the first structure part along the extension direction of the needle head through mutual slip matching; the third limit structure is a protrusion structure formed on the first structure part, the protrusion structure has an inclined plane engaging with outer surface of the first structure part, the inclined plane locates at a side adjacent to the second end of the needle head, the protrusion structure has a recess groove at a top and the fourth limit structure is an elastic button at a side of the second structure part that is away from the second end of the needle head, the elastic button has an elastic button chunk; the inclined plane of the button is adapted to slip match with the elastic button chunk to elastically deform the elastic button, and the elastic button chunk is adapted to be clamped in the recess groove of the protrusion structure through elastic recovery of the elastic button.

7. The needle device of claim 1, wherein the second limit mechanism comprises a first blocking portion, a second blocking portion, a third blocking portion and an elastic button; the first blocking portion and the second blocking portion are arranged on an upper surface of the first structure part, the elastic button is arranged on an upper surface of the second structure part, the third blocking portion is arranged on a lower surface of the second structure part, the second blocking portion prevents the third blocking portion from further moving when the elastic button moves to a position in front of the first blocking portion.

8. The needle device of claim 1, wherein the first structure part is a first sleeve part, the first sleeve part sheathes the needle base; the second structure part is a second sleeve part, the second sleeve part sheathes the first sleeve part;

or a length of the needle base is larger than 2 mm, a length of the first structure part is larger than 2 mm, and a length of the second structure part is larger than 2 mm.

9. The needle device of claim 1, wherein the first structure part is opened at the first side of the installation portion;

or the installation portion has a top surface which is opposite to the first side of the installation portion and is away from the skin during use, the first structure part has a bottom surface which is adjacent to the skin during use, the bottom surface of the first structure part is located between the first side of the installation portion and the top surface of the installation portion.

10. The needle device of claim 1, wherein the second structure part has an opened structure at the first side of the installation portion, the bottom structure is an edge of the opened structure of the second structure part;

or a cushion is arranged at a bottom of the second structure part, the bottom structure is the cushion, a bottom of the cushion is a flat surface, and the installation portion and the first structure part are arranged inside a space surrounded by the second structure part;

or the cushion is arranged at the bottom of the second structure part, the bottom structure is the cushion, the bottom of the cushion is the flat surface, and the installation portion and the first structure part are arranged inside the space surrounded by the second structure part; a clamping portion is arranged at lower section of the second structure part, and the cushion is clamped by the clamping portion;

or the cushion is arranged at the bottom of the second structure part, the bottom structure is the cushion, the bottom of the cushion is the flat surface, and the installation portion and the first structure part are arranged inside the space surrounded by the second structure part, and the second structure part comprising the cushion is integrally formed;

or the cushion is arranged at bottom of the second structure part, the bottom structure is the cushion, the bottom of the cushion is the flat surface, and the installation portion and the first structure part are arranged inside the space surrounded by the second structure part, and a vertical distance between the needle head and the bottom of the cushion is larger than 0.05 mm;

or the second structure part is a sleeve piece, the second structure part has the flat bottom at the first side of the installation portion, the bottom structure is the flat bottom segment of the second structure part;

or the second structure part is the sleeve piece, the second structure part has the flat bottom at the first side of the installation portion, the bottom structure is the flat bottom segment of the second structure part, and an exterior of the flat bottom segment of the second structure part is provided with convex portions extending parallel to the first side, and a concave portion extending parallel to the first side is formed between adjacent convex portions;

or the bottom structure is a soft structure;

or inner wall of the bottom structure slip matches with the first side of the installation portion.

11. The needle device of claim 1, wherein a first connection structure and a second connection structure which are mutually slip matched are respectively formed on the needle base and the first structure part, and a third connection structure and a fourth connection structure which are mutually slip matched are respectively formed on the first structure part and the second structure part;

or the first connection structure and the second connection structure which are mutually slip matched are respectively formed on the needle base and the first structure part, and the third connection structure and the fourth connection structure which are mutually slip matched are respectively formed on the first structure part and the second structure part, and the first connection structure and the second connection structure are respectively a first slide railway and a first slide track which are arranged along the extension direction of the needle head, or the first connection structure and the second connection structure are respectively the first slide track and the first slide railway which are arranged along the extension direction of the needle head, the third connection structure and the fourth connection structure are respectively a second slide railway and a second slide track which are arranged along the extension direction of the needle head, or the third connection structure and the fourth connection structure are respectively the second slide track and the second slide railway which are arranged along the extension direction of the needle head.

12. The needle device of claim 1, wherein a pressing portion is arranged on an upper surface of the second structure part.

13. The needle device of claim 1, wherein the needle base is provided with an operating handle, the operating handle is provided with at least one wing portion;

or the needle base is provided with the operating handle, the operating handle is provided with the at least one wing portion, and the needle device further comprises one wing portion, the wing portion is located at one side of the needle base;

or the needle base is provided with the operating handle, the operating handle is provided with the at least one wing portion, and the needle device further comprises two wing portions, the wing portions are located at both sides of the needle base separately;

or the needle base is provided with the operating handle, the operating handle is provided with the at least one wing portion, and the operating handle is sleeved with the needle base, or the operating handle is integrally formed with the needle base, or the operating handle is clamped by the needle base;

or the needle base is provided with the operating handle, the operating handle is provided with the at least one wing portion, and the operating handle further comprises a bent portion, the bent portion is arranged between the wing portion and the needle base.

14. The needle device of claim 1, wherein both of the first structure part and the second structure part are slot-shaped;

or the needle device comprises a plurality of first structure parts, the plurality of first structure parts are arranged by layer and are mutually slip matching along the extension direction of the needle head, a third limit mechanism is arranged between mutual slip matching first structure parts to prevent the first structure parts being separated along the extension direction of the needle head, an innermost first structure part slip matches with the needle base, an outermost first structure part slip matches with the second structure part;

or the needle device is an intravenous needle, a blood taking needle, a remaining needle or an injection needle.

* * * * *